(12) United States Patent
Leleu et al.

(10) Patent No.: US 6,344,591 B2
(45) Date of Patent: *Feb. 5, 2002

(54) MALTITOL CRYSTALS OF PARTICULAR FORMS, CRYSTALLINE COMPOSITIONS CONTAINING THEM AND PROCESSES FOR THEIR PREPARATION

(75) Inventors: Jean-Bernard Leleu, Lestrem; Patrick Haon, Haguenau; Pierrick Duflot, Lacouture; Philippe Looten, Lambersart, all of (FR)

(73) Assignee: Roquette Freres, Lestrem (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/160,133

(22) Filed: Sep. 25, 1998

(30) Foreign Application Priority Data

Sep. 26, 1997 (FR) .............................. 97 12035

(51) Int. Cl.$^7$ .......................... C07C 31/18; C07H 1/00
(52) U.S. Cl. ..................... 568/852; 536/4.1; 536/18.5; 127/40; 127/46.1
(58) Field of Search ................ 536/4.1, 18.5; 568/852; 127/40, 46.1

(56) References Cited

U.S. PATENT DOCUMENTS

| 3,915,736 A | 10/1975 | Oyamada et al. ........... 426/213 |
|---|---|---|
| 3,918,986 A | 11/1975 | Hiraiwa ........................ 127/29 |
| 4,248,895 A | 2/1981 | Stroz et al. .................. 426/658 |
| 4,408,041 A | 10/1983 | Hirao et al. |
| 4,429,122 A | 1/1984 | Zupancic ..................... 536/124 |
| 4,511,654 A | 4/1985 | Rohrbach et al. ............. 435/95 |
| 4,831,129 A | 5/1989 | Serpelloni et al. ........... 536/4.1 |
| 4,846,139 A | * 7/1989 | Devos et al. ................. 127/40 |
| 4,849,023 A | 7/1989 | Devos et al. ............... 568/872 |

FOREIGN PATENT DOCUMENTS

| EP | 0 735 042 | 10/1996 |
|---|---|---|
| EP | 741140 | * 11/1996 |
| GB | 1.383.724 | 2/1975 |
| JP | 48.61665 | 8/1973 |
| JP | 49.87619 | 8/1974 |
| JP | 49.110620 | 10/1974 |
| JP | 57.47680 | 4/1975 |
| JP | 50.59312 | 5/1975 |
| JP | 50.129769 | 10/1975 |
| JP | 51.113813 | 10/1976 |
| JP | 58.58145 | 9/1983 |
| WO | WO 95/10627 | 4/1995 |

OTHER PUBLICATIONS

S. Ohno, et al: X–Ray crystal structure of maltitol–carbohydrate Research (Jan. 1, 1982), vol. 108, Amsterdam pp. 163–171.

* cited by examiner

*Primary Examiner*—Gary Geist
*Assistant Examiner*—Everett White
(74) *Attorney, Agent, or Firm*—Henderson & Sturm LLP

(57) ABSTRACT

The invention concerns modified maltitol crystals of particular forms, one pyramidal, the other prismatic. It further concerns crystalline compositions containing them and processes for their preparation.

7 Claims, 4 Drawing Sheets

MALTITOL CRYSTALS OF PARTICULAR FORMS, CRYSTALLINE COMPOSITIONS CONTAINING THEM AND PROCESSES FOR THEIR PREPARATION

The present invention concerns maltitol crystals of particular forms and crystalline compositions containing them. It also relates to a particular process for obtaining these crystals and compositions.

For a very long time, maltitol was presented only in the form of low content syrups.

Then, maltitol was marketed in the form of amorphous and impure powders.

To the knowledge of the Applicant company, it was only about 1980 that prominence was given to maltitol crystals. Previously, this polyol was not known as forming crystals easily.

The only crystalline form known up till now for maltitol is the anhydrous form, which is subject to wide-ranging patent protection on behalf of the HAYASHIBARA company (U.S. Pat. No. 4,408,041).

The so-called "massé" techniques on the one hand and those of water crystallisation on the other, are today almost the only processes in industrial use. The products thus obtained are of very variable crystallinity and are not all particularly well suited to certain applications such as chewing-gum or chocolate.

On the other hand, there are other applications where these products are not totally satisfactory. This is the case for example when it is required to use maltitol to replace saccharose and lactose in pharmaceutical dry forms such as capsules, medicines of the soluble powder type, tablets and food preparations in powdered form to be dissolved. This is also the case when it is required to effect the same kind of substitution in sweetened foods such as powdered drinks, desserts, cake preparations or chocolate-flavoured or vanilla-flavoured breakfast powders.

It is noted for these particular applications, particularly for pseudo-crystalline maltitol powders obtained by the "massé" technique and to a lesser degree for crystalline maltitol powders obtained by crystallisation in water, that these have one or more defects in particular for example those of not flowing easily, of being liable to cake or to knot together, of dissolving only very slowly in water, of being bad vehicles for compression or of not meeting the criteria for identification and purity set by different pharmacopoeias.

In its wish to improve on the prior art, the Applicant company has sought to perfect maltitol compositions which do not have the flow, caking, dissolving or compression defects presented by known maltitol powders. Admittedly, it might have been thought possible to meet the identified need with other polyols. But, this is demonstrably not so since none of them has characteristics of solubility, hygroscopicity, sweetened flavour and fusion as close to saccharose as maltitol.

And it is while working to perfect these compositions that the Applicant company was able to isolate, in a surprising and unexpected way, two particular forms of maltitol crystals, one bipyramidal and the other prismatic.

It is to the credit of the Applicant company that it has succeeded, after conducting extensive research, in explaining the existence of these two forms of maltitol crystals. It has indeed demonstrated that, against all expectation, the form of the maltitol crystals was a function of the maltotriitol content of a maltitol syrup intended for crystallisation. The Applicant company has noted that by controlling the maltotriitol content of a maltitol syrup, it was possible to direct the form of the maltitol crystals towards one or other of the forms or towards a mix of the two forms, when this maltitol syrup is subjected to a crystallisation stage.

As a result, according to a first aspect, the invention relates to modified maltitol crystals, characterised in that they are bipyramidal in form including two regular tetrahedrons juxtaposed by their square section base with sides of about 50 to 500 μm, thus constituting regular octahedrons with edge length of about 50 to 500 μm.

According to a second aspect, the invention also concerns modified maltitol crystals, characterised in that they are prismatic in form ending with plane faces constituting a tetrahedron, and in that they are 100 to 400 μm long and about 20 to 100 μm wide.

The forms of crystallisation (bipyramidal or prismatic) inevitably have significant repercussions both for manufacture and for applications. Thus, a semi-crystallised maltitol mass, including a certain percentage of prismatic crystals is more viscous than a mass including the same percentage of bipyramidal crystals, all things being equal in other respects, and this particularly when the crystals are of significant size.

Therefore to prepare atomised maltitol, it is preferable to accept suspensions which are very low in maltotriitol and additionally including bipyramidal rather than prismatic crystals so as to avoid caking. In other respects, the use of bipyramidal maltitol crystals proves advantageous in the production of chocolate (more thickened mass before refining), of chewing-gums (possibility of retaining a flexible texture with a large amount of powdered maltitol), of pharmaceutical dry forms (greater consistency of flow) etc.

On the other hand, a prismatic form is more compressible and enables low crystal content caking, as is sometimes required (chewing-gums, chewing-gum centres to be sugar coated).

Other features and advantages of the invention will become fully apparent on reading the following description, made by reference to the appended drawings, in which.

The invention therefore concerns first of all the bipyramidal and prismatic crystals illustrated in FIGS. 1 to 4.

The observations were carried out with the help of a JEOL 5410 scanning electron microscope, after gold-plating the crystals with a JEOL JFC 1100 E metal sprayer (coating thickness 100 Angstroms).

The crystals were observed under a voltage of 2 and 5 kV. The photographs were taken on the microscope with an enlargement of 350 times (FIG. 1), 500 times (FIG. 2), 50 times (FIG. 3) and 200 times (FIG. 4), then blown up during printing. However, there is a scale inscribed on the photograph to show the actual size of the crystals.

Figure 1:
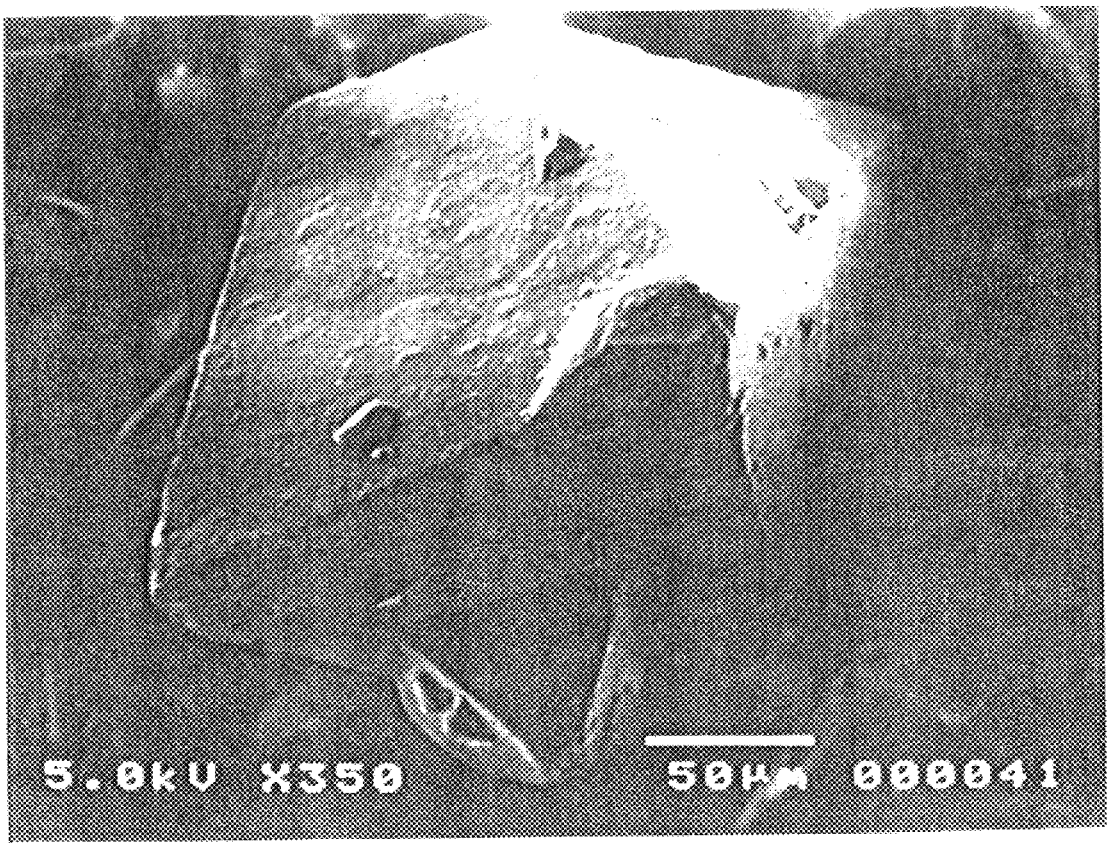
FIGS. 1 and 2 show photographs by scanning electron microscope of crystals of bipyramidal form in compliance with the invention.
Figure 2:
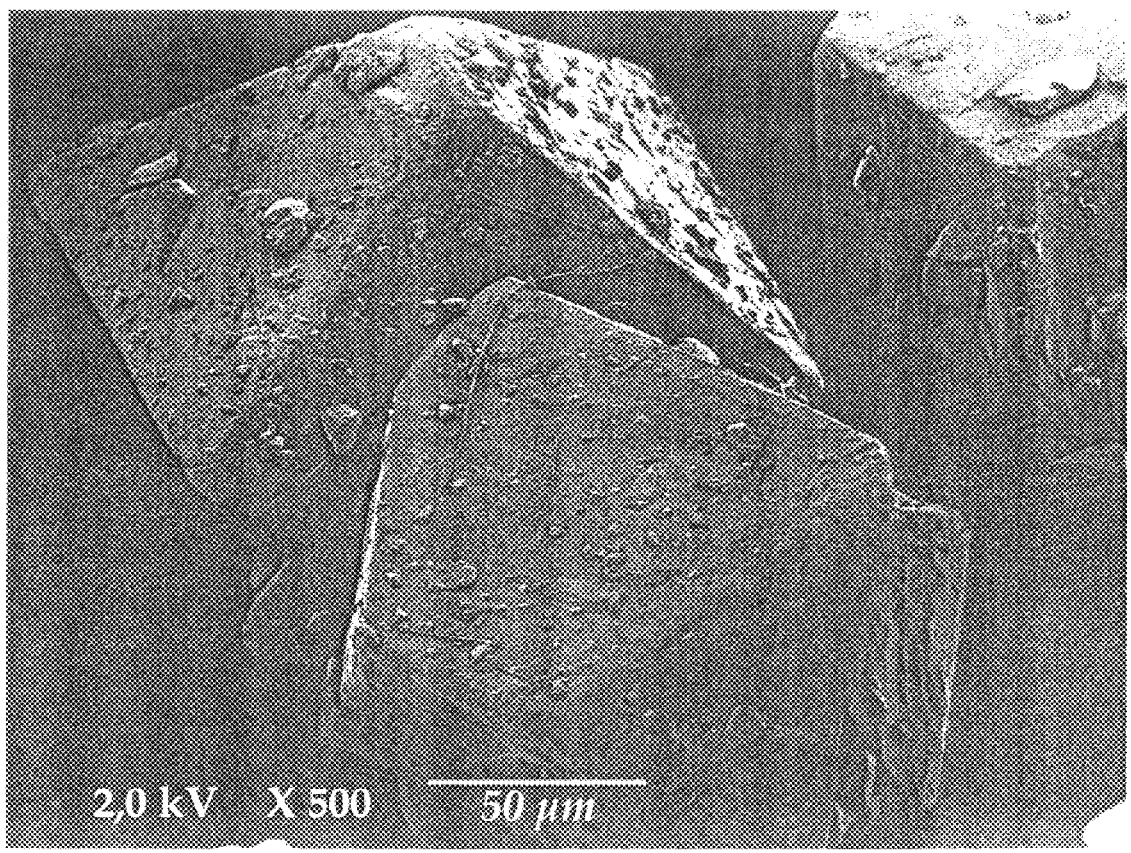

The crystals in FIGS. 1 and 2 are of massive, bipyramidal form. More exactly, they have the form of two regular tetrahedrons, juxtaposed by their square section base, with sides from 50 to 500 μm approximately, thus constituting regular octahedrons with edge length of 50 to 500 μm approximately.

Figure 3:
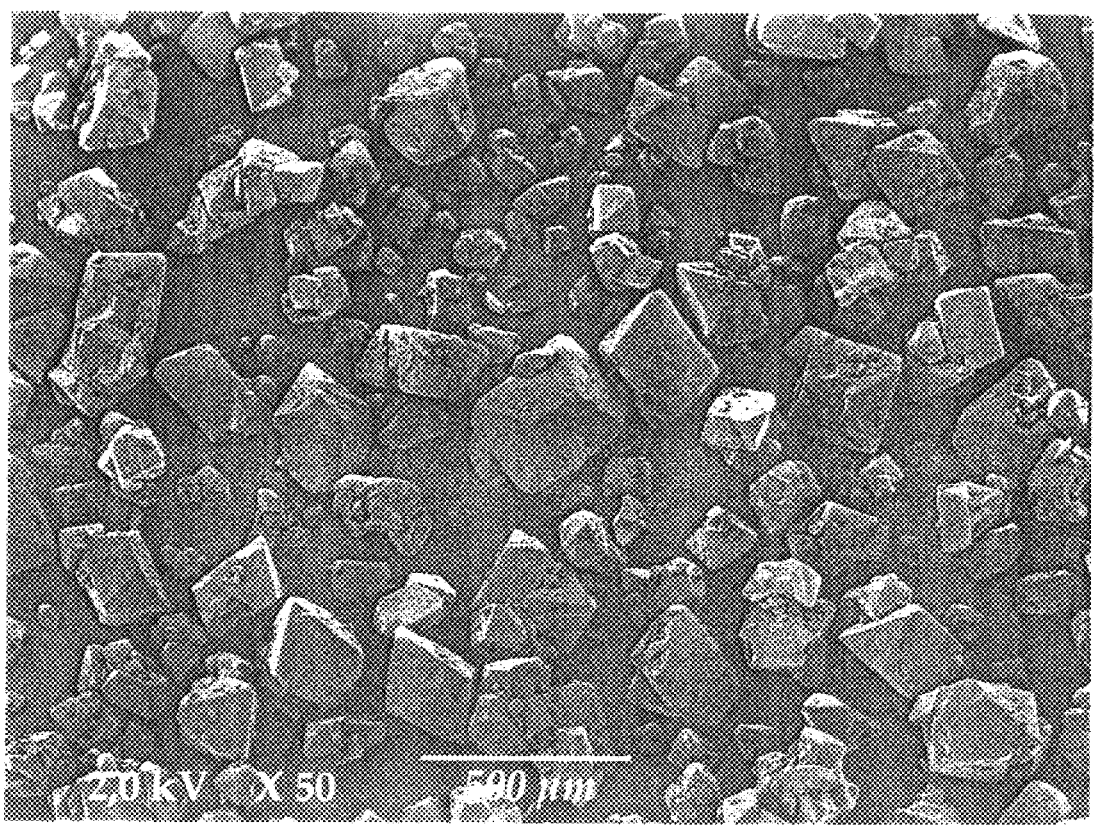
FIG. 3 shows a less enlarged photograph by scanning electron microscope of crystals identical to those in FIGS. 1 and 2.

FIG. 3 shows that crystals in compliance with the invention are not caked together or arranged in small aggregated clusters but are on the contrary fully dissociated and individualised in relation to each other.

Figure 4:
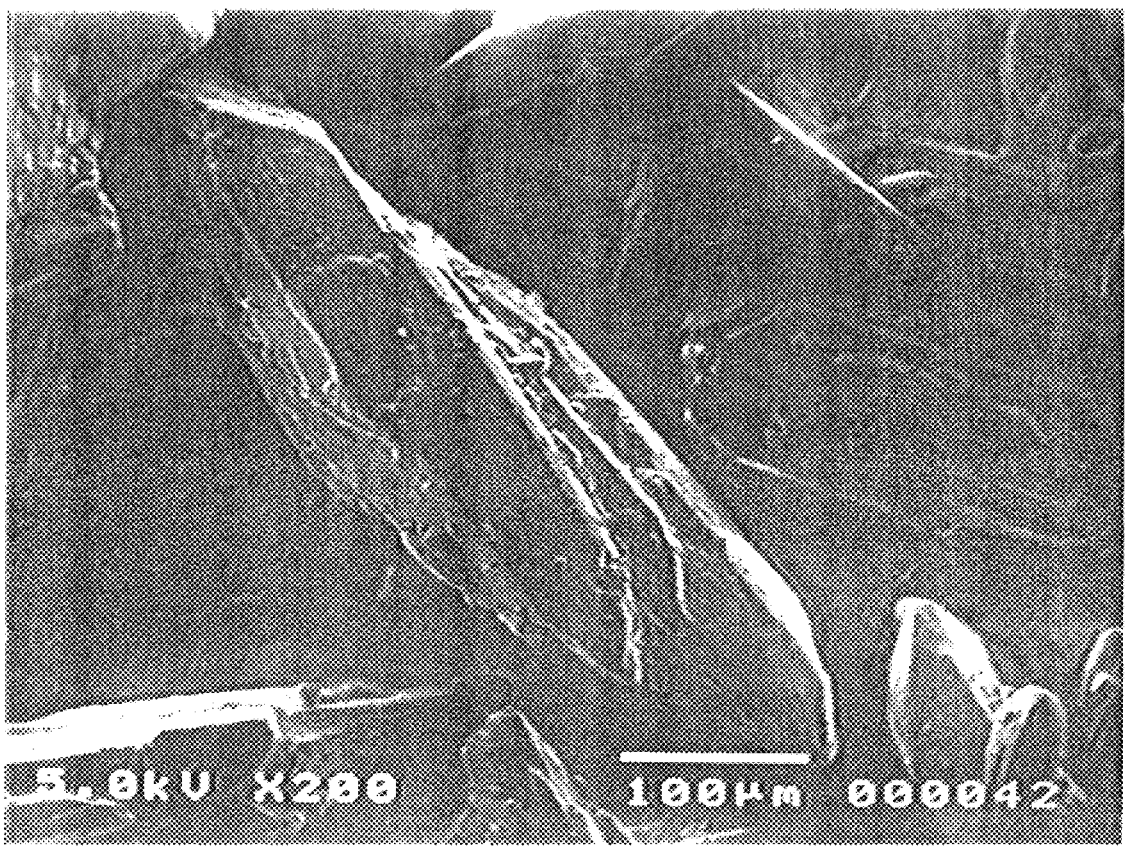
FIG. 4 shows a photograph by scanning electron microscope of a crystal of prismatic form in compliance with the invention.

The crystal in FIG. 4 looks like a rod with a pointed end. More exactly, it is prismatic in form and longer than it is wide (approximately 5 times longer than it is wide), ending in plane faces constituting a tetrahedron. This rod is approximately 100 to 400 μm long by 20 to 100 μm wide.

The invention further concerns a crystalline maltitol composition, characterised in that it is constituted:

either by bipyramidal crystals complying with the invention;
or by prismatic crystals complying with the invention;
or by both bipyramidal and prismatic crystals.

The first essential characteristic of maltitol compositions in accordance with the invention lies in the fact they are crystallised, which gives them very high stability in relation to humidity. As a result they have only a slight tendency to cake or to knot together. So they are easy to use and it is not imperative to take draconian precautions to guard against this danger.

These crystalline maltitol compositions all have a maltitol content greater than or equal to 87%, preferably greater than or equal to 92%, and more preferentially greater than or equal to 96%, and advantageously have a reduced content of maltosyl-1.6 maltitol.

What essentially differentiates them from each other is the maltotriitol content.

Thus, when the crystalline maltitol composition is constituted by maltitol crystals of bipyramidal form, it has a maltotriitol content, by weight of dry matter, of less than 1%.

When the crystalline maltitol composition is constituted by maltitol crystals of prismatic form, it has a maltotriitol content, by weight of dry matter, greater than or equal to 4%.

And when the crystalline maltitol composition is constituted by maltitol crystals of both bipyramidal and prismatic form, it has a maltotriitol content, by weight of dry matter, of between 1 and 4%.

The concept of content must be understood, in the case of the present invention, as corresponding to the percentage of maltitol expressed as dry/dry weight in relation to the total carbohydrates present in the crystalline maltitol composition. The carbohydrates may be polyols such as in particular sorbitol, maltotriitol and maltotetraitol.

The crystalline maltitol compositions complying with the invention may contain, without their presence significantly altering the crystallinity of these compositions, certain substances such as for example strong sweeteners, colouring agents, pigments, scents, flavourings, vitamins, minerals, trace elements, active pharmaceutical or veterinary ingredients, esters of fatty acids, organic or inorganic acids and their salts, proteinic matter such as proteins, amino acids and enzymes.

The crystalline maltitol compositions are likely to be obtained by crystallisation of a maltitol syrup with maltitol content greater than or equal to 87%, preferably greater than or equal to 92%, and more preferentially greater than or equal to 96%, and a maltotriitol content which, according to the composition which it is wished to obtain, is less than 1%, between 1 and 4%, or more than 4% by weight of dry matter.

One of the essential characteristics of the invention is therefore to vary the maltotriitol contents of the maltitol syrups to be crystallised while advantageously retaining a reduced content of maltosyl-1,6 maltitol.

It is for this reason that the invention further concerns a process to direct the form of the maltitol crystals, characterised in that it consists in controlling the maltotriitol content of the maltitol syrup to be crystallised. This control of the maltotriitol content of the maltitol syrup to be crystallised may be carried out upstream and/or downstream of the crystallisation stage.

Upstream of the crystallisation stage:
during manufacture of the maltose syrup by using enzymes which hydrolyse the maltotriose, and/or:
by carrying out a molecular sieving of the maltose syrup intended for hydrogenation then crystallisation, and/or:
by carrying out a molecular sieving of the maltitol syrup intended for crystallisation and/or:
by carrying out an enzymatic hydrolysis of the maltitol syrup intended for crystallisation.

Downstream of the crystallisation stage:
by redissolving the crystalline maltitol composition in water and by carrying out a molecular sieving on the syrup thus obtained and/or an enzymatic hydrolysis and/or
by redissolving the crystalline maltitol composition in water and adding to it the amounts of maltotriitol required to obtain, after recrystallisation, a new crystalline maltitol composition complying with the invention with the required maltotriitol content.

All these possibilities for controlling the maltotriitol content may be used singly or in combination with each other.

From what precedes, it therefore follows that the process for directing the form of the maltitol crystals, in compliance with the invention, offers great flexibility in use. Indeed it enables switching equally well from bipyramidal form crystals to prismatic form crystals and vice versa.

To prepare the maltitol syrup which enables, after crystallisation, the compositions complying with the invention to be obtained, the process described below or an equivalent process is used.

The first step in the process is known per se. It consists in liquefying a starch slurry which may be of any botanical origin: it may derive from corn, maize or potato for example.

This starch or flour slurry has acid added in the case of a so-called acid liquefaction, or an α-amylase added in the case of enzymatic liquefaction.

In the process complying with the invention, it is preferred to carry out a controlled hydrolysis of the starch slurry so as to obtain a liquefied starch slurry with a low transformation rate. In this way, conditions of temperature, of pH, of enzyme and calcium content, known to the professional, are determined in such a way that they enable a DE(Dextrose Equivalent) to be obtained of less than 10, preferably less than 6, and more particularly less than 4.

Preferably, the liquefaction stage is conducted in two sub-stages, the first consisting in heating the starch slurry, for a few minutes and at a temperature of between 105 and 108° C., in the presence of an α-amylase (TERMAMYL$^R$ 120L type marketed by the NOVO company) and a calcium based activator, the second consisting in heating the starch slurry thus treated to a temperature of between 95 and 100° C. for one to two hours.

Once the liquefaction stage is complete, in the conditions of dry matter content, of pH, of enzyme and calcium content that are well known to the professional, the next step is the inhibition of the α-amylase. This inhibition of the α-amylase may preferably be carried out thermally by initiating at the end of the liquefaction process a thermal shock lasting a few seconds at a temperature exceeding or equal to 130° C.

Following this the saccharification stage is carried out. During this stage, the liquefied starch slurry is first subjected to the action of a maltogenic α-amylase, such as that marketed by the NOVO company, under the name Maltogénase®. During this first saccharification stage, the maltogenic α-amylase can be added in a single dose or in several doses.

At this stage of the process, it is already possible to control the maltotriose content (which after hydrogenation leads to maltotriitol) formed during the hydrolysis of the starch, by adjusting the amount of maltogenic α-amylase as a function of the maltotriose content and therefore of the form of the maltitol crystals that it is wished to obtain.

The next step, after allowing the maltogenic α-amylase to react, is the saccharification of the liquefied starch slurry by means of a β-amylase such as that marketed by the GENENCOR company under the name SPEZYME$^R$ BBA 1500.

During these stages, it is appropriate to combine with the maltogenic action enzymes (maltogenic α-amylase and β-amylase) an enzyme which specifically hydrolyses the α-1,6 starch bonds. This addition of a disconnecting enzyme enables on the one hand hydrolysis reactions to be accelerated without simultaneously accelerating reversion reactions and, on the other hand, the amount of strongly connected oligosaccharides normally resistant to the action of maltogenic enzymes to be reduced.

This disconnecting enzyme can be added at the same time as the maltogenic α-amylase is added or at the same time as the β-amylase is added.

This disconnecting enzyme is selected from the group constituted by the pullulanases and the isoamylases.

The pullulanase is for example that marketed by the ABM company under the name PULLUZYME$^R$.

The isoamylase is for example that marketed by the HAYASHIBARA company.

The process is implemented to advantage in the presence of isoamylase for which the Applicant company has noted that it not only enabled a maltose syrup with a higher maltose content to be obtained than by using a pullulanase, but it also enabled a maltose syrup with a reduced content of maltosyl-1,6 maltose and therefore of maltosyl-1,6 maltitol after hydrogenation to be obtained.

The saccharification stage can also be conducted totally or partially in the presence of fungal α-amylase.

At the end of saccharification, it is possible to add a little α-amylase, which generally improves the subsequent filtration stages. The amounts and conditions of action of the different enzymes used in the liquefaction and saccharification stages of the starch slurry are generally those which are recommended for the hydrolysis of starch and are well known to the person skilled in the art.

Saccharification is carried out until the maltose hydrolysate contains at least 87%, preferably at least 92%, and more preferentially at least 96% by weight of maltose.

The hydrolysate thus saccharified is then filtered through a pre-coated filter or by micro-filtration through membranes, then de-mineralised.

At this stage in the process, it may be possible to carry out on the saccharified and purified hydrolysate, a stage of maltose crystallisation or molecular sieving, this molecular sieving stage enabling the maltotriose content of the maltose syrup to be controlled, i.e. to more or less deplete, or not at all, the maltose syrup of maltotriose. This molecular sieving stage may thus also enable the recovery of:

either a first fraction enriched in maltose and higher oligosaccharides and a second fraction enriched in glucose;

or a first fraction enriched in higher oligosaccharides and a second fraction enriched in maltose and glucose;

or, lastly, a first fraction enriched in higher oligosaccharides, a second fraction enriched in maltose and a third fraction enriched in glucose.

This molecular sieving stage may consist, for example, of a chromatographic separation stage or a separation by membrane stage.

The chromatographic fractionation stage is conducted in a way known per se, discontinuously or continuously (simulated fluid bed), on adsorbents of the cationic resin type, or on highly acid zeolites, preferentially charged with the help of alkaline or alkaline-earth ions such as calcium or magnesium but more preferentially with the help of sodium ions.

Instead and in place of the chromatographic separation stage, it is possible to implement a separation stage by nano-filtration by membranes. Membranes of various pore diameters are manufactured from a number of polymers and copolymers of the polysulphone, polyamide, polyacrylonitrate, polycarbonate, polyphurane types, etc.

Examples of the use of such membranes are described particularly in the documents U.S. Pat. Nos. 4,511,654, 4,429,122 and WO-A-95/10627.

The maltose hydrolysate thus obtained may then be easily hydrogenated catalytically.

The hydrogenation of such a hydrolysate is carried out in compliance with the rules of the art which lead for example to the production of sorbitol from glucose.

For this stage ruthenium based catalysts can be used as well as RANEY nickel catalysts. The use of RANEY nickel catalysts is however preferred since they are less expensive.

In practice, from 1 to 10% by weight of catalyst compared with the dry matter of the hydrolysate subjected to hydrogenation is used. Hydrogenation is carried out preferably on a hydrolysate the dry matter of which is between 15 and 50%, in practice in the area of 30 to 45%, at between 20 and 200 bars of hydrogen pressure. It can be carried out continuously or discontinuously.

When the operation is discontinuous, the hydrogen pressure used is generally between 30 and 60 bars and the temperature at which hydrogenation occurs is between 100 and 150° C. Care is also taken to maintain the pH of the hydrogenation medium by the addition of sodium hydroxide or sodium carbonate for example, but without exceeding a pH of 9.0. This way of proceeding enables the appearance of cracking or isomerisation products to be avoided.

The reaction is stopped when the reducing sugars content of the reaction medium has dropped below 1%, preferably even below 0.5% and more particularly below 0.1%.

After the reaction medium has cooled, the catalyst is eliminated by filtration and the maltitol syrup thus obtained is demineralised on cationic and anionic resins. At this stage, the syrups contain at least 85% maltitol.

According to a first version of the process, a series of steps is applied to the maltitol syrup obtained in the preceding hydrogenation stage as follows:

possibly carrying out a chromatographic fractionation, known per se, so as to obtain a maltitol rich fraction and a more or less rich maltotriitol fraction as a function of the form of crystals required;

concentrating the maltitol rich fraction;

crystallising and separating the formed maltitol crystals;

recycling the crystallisation mother-liquors upstream of the chromatographic fractionation stage.

According to a second version of the process, a series of steps is applied to the maltitol syrup obtained in the preceding hydrogenation stage as follows:

concentrating the maltitol syrup;

crystallising and separating the formed maltitol crystals.

According to a third version of the process, a series of steps is applied to the maltitol syrup obtained in the preceding hydrogenation stage as follows:

possibly carrying out an enzymatic hydrolysis of the maltitol syrup, by means for example of an amyloglucosidase whether immobilised or not so as to convert any possibly present maltotriitol into maltitol;

concentrating the maltitol syrup thus obtained;

crystallising and separating the formed maltitol crystals.

According to another version of the process complying with the invention, a series of steps is applied to the maltose hydrolysate obtained after saccharification as follows:

possibly carrying out a chromatographic fractionation, known per se, so as to obtain a maltose rich and more or less maltotriose rich fraction;

hydrogenating the maltose rich fraction;

crystallising and separating the formed maltitol crystals.

The invention will now be described with the help of the following example provided solely by way of illustration and non-restrictively.

EXAMPLE

1. Test conditions

The syrup to be crystallised is concentrated to 80% dry matter, placed in a laboratory crystallising dish and stabilised at a temperature of 50° C., then an initial nucleus of MALTISORB$^R$ (crystallised maltitol marketed by the Applicant company) at the rate of 1%/dry matter, is added and the crystallising dish is cooled under slow stirring to 20° C., at the rate of 0.3° C. per hour. After spinning and clearing with ethanol, the crystals are dried and observed under a scanning electron microscope.

2. Results

Different bases are used; their composition and the form of the crystals obtained are summarised in the following table.

| COMPOSITION | CRYSTAL APPEARANCE |
|---|---|
| DP2H > 99% | homogeneous, bipyramidal in form |
| DP2H: 93 · 5% | |
| DP3H: 3 · 8% | heterogeneous, bipyramidal |
| Sup.: 2 · 7% | and prismatic in form |
| DP1H: 5 · 2% | |
| DP2H: 90 · 1% | homogeneous, |
| DP3H: 0 · 9% | bipyramidal in form |
| DP4H: 3 · 8% | |
| DP2H: 96% | homogeneous, |
| DP3H: 4% | prismatic in form |

DP1H = sorbitol
DP2H = maltitol
DP3H = maltotriitol
DP4H = maltotetraitol
Sup. = maltotetraitol and superior homologues

What is claimed is:

1. Modified maltitol crystals, being bipyramidal in form comprising two regular tetrahedrons juxtaposed by their square section base with sides of 50 to 500 μm approximately, thus constituting regular octahedrons with edge length of approximately 50 to 500 μm.

2. A crystalline maltitol composition, comprising essentially maltitol crystals according to claim 1 and having a maltitol content greater than or equal to 87% and a maltotriitol content by weight of dry matter, lower than 1%.

3. A crystalline maltitol composition according to claim 2 having a maltitol content greater than or equal to 92%.

4. A crystalline maltitol composition according to claim 3 having a maltitol content greater than or equal to 96%.

5. A manufacturing process of maltitol crystals in accordance with claim 1, comprising the following steps:

liquefaction of a starch slurry, saccharification of the slurry to obtain a maltose hydrolysate containing 87% by weight of maltose, filtration and de-mineralisation of the maltose hydrolysate, hydrogenation of the maltose hydrolysate to obtain a maltitol syrup having a maltitol content greater than or equal to 87% and a maltotriitol content lower than 1% by weight of dry matter, crystallization of the syrup and separation of the formed maltitol crystals.

6. A manufacturing process according to claim 5, wherein the maltitol syrup has a maltitol content greater than or equal to 92%.

7. A manufacturing process according to claim 6, wherein the maltitol syrup has a maltitol content greater than or equal to 96%.

* * * * *

(12) EX PARTE REEXAMINATION CERTIFICATE (9067th)

United States Patent
Leleu et al.

(10) Number: US 6,344,591 C1
(45) Certificate Issued: *Jun. 12, 2012

(54) MALTITOL CRYSTALS OF PARTICULAR FORMS, CRYSTALLINE COMPOSITIONS CONTAINING THEM AND PROCESSES FOR THEIR PREPARATION

(75) Inventors: Jean-Bernard Leleu, Lestrem (FR); Patrick Haon, Haguenau (FR); Pierrick Duflot, Lacouture (FR); Philippe Looten, Lambersart (FR)

(73) Assignee: Roquette Freres, Lestrem (FR)

( * ) Notice: This patent issued on a continued prosecution application filed under 37 CFR 1.53(d), and is subject to the twenty year patent term provisions of 35 U.S.C. 154(a)(2).

Reexamination Request:
No. 90/011,953, Oct. 13, 2011

Reexamination Certificate for:
Patent No.: 6,344,591
Issued: Feb. 5, 2002
Appl. No.: 09/160,133
Filed: Sep. 25, 1998

(30) Foreign Application Priority Data

Sep. 26, 1997 (FR) .............................. 97 12035

(51) Int. Cl.
*A23L 1/236* (2006.01)
*A61K 47/26* (2006.01)
*C07B 63/00* (2006.01)
*C07H 15/04* (2006.01)

(52) U.S. Cl. ................... 568/852; 127/40; 127/46.1; 536/18.5; 536/4.1

(58) Field of Classification Search .................. None
See application file for complete search history.

(56) References Cited

To view the complete listing of prior art documents cited during the proceeding for Reexamination Control Number 90/011,953, please refer to the USPTO's public Patent Application Information Retrieval (PAIR) system under the Display References tab.

*Primary Examiner* — Gary Kunz

(57) ABSTRACT

The invention concerns modified maltitol crystals of particular forms, one pyramidal, the other prismatic. It further concerns crystalline compositions containing them and processes for their preparation.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 is confirmed.

Claims 5-7 were not reexamined.

\* \* \* \* \*